US011234663B2

United States Patent
Proksa

(10) Patent No.: US 11,234,663 B2
(45) Date of Patent: Feb. 1, 2022

(54) APPARATUS FOR GENERATING MULTI ENERGY DATA FROM PHASE CONTRAST IMAGING DATA

(71) Applicant: KONINKLIJKE PHILIPS N.V., Eindhoven (NL)

(72) Inventor: Roland Proksa, Neu Wulmstorf (DE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 0 days.

(21) Appl. No.: 16/348,269

(22) PCT Filed: Nov. 9, 2017

(86) PCT No.: PCT/EP2017/078709
§ 371 (c)(1),
(2) Date: May 8, 2019

(87) PCT Pub. No.: WO2018/091344
PCT Pub. Date: May 24, 2018

(65) Prior Publication Data
US 2019/0313991 A1 Oct. 17, 2019

(30) Foreign Application Priority Data
Nov. 16, 2016 (EP) ................................ 16199050

(51) Int. Cl.
*A61B 6/00* (2006.01)

(52) U.S. Cl.
CPC ............ *A61B 6/484* (2013.01); *A61B 6/482* (2013.01); *A61B 6/5211* (2013.01); *A61B 6/582* (2013.01)

(58) Field of Classification Search
CPC ....... A61B 6/482; A61B 6/484; A61B 6/5211; A61B 6/582; G01N 23/087; G01N 23/20083
See application file for complete search history.

(56) References Cited

U.S. PATENT DOCUMENTS

| 9,761,024 | B1 | 9/2017 | Proksa |
| 9,842,414 | B2 | 12/2017 | Koehler |
| 10,332,281 | B2 * | 6/2019 | Chen ...................... G06T 5/002 |
| 11,054,304 | B2 | 7/2021 | Ozawa |

(Continued)

FOREIGN PATENT DOCUMENTS

| WO | 2013/104966 | 7/2013 |
| WO | 2015014677 | 2/2015 |

(Continued)

OTHER PUBLICATIONS

International Search Report and Written Opinion dated Feb. 1, 2018, for International Application No. PCT/EP2017/078709 filed Nov. 9, 2017.

*Primary Examiner* — Dani Fox
*Assistant Examiner* — Soorena Kefayati
(74) *Attorney, Agent, or Firm* — Larry Liberchuk

(57) ABSTRACT

An apparatus provides phase contrast X-ray image data of a region of interest of an object. Attenuation X-ray image data of the region of interest of the object is also provided. A first basis data set is generated from the phase contrast X-ray image data. A second basis data set is generated from the phase contrast X-ray image data and the attenuation X-ray image data.

11 Claims, 4 Drawing Sheets

(56) References Cited

U.S. PATENT DOCUMENTS

| | | | | |
|---|---|---|---|---|
| 2005/0119563 A1* | 6/2005 | Francke | | A61B 6/5247 600/427 |
| 2007/0161885 A1* | 7/2007 | Kimchy | | A61B 5/42 600/407 |
| 2008/0135789 A1* | 6/2008 | Du | | A61B 6/482 250/580 |
| 2008/0253504 A1* | 10/2008 | Proksa | | A61B 6/032 378/5 |
| 2012/0134531 A1* | 5/2012 | Zhang | | A61B 6/032 382/100 |
| 2013/0216113 A1* | 8/2013 | O'Connor | | G06T 11/60 382/128 |
| 2014/0079184 A1* | 3/2014 | Das | | A61B 6/484 378/62 |
| 2014/0133729 A1* | 5/2014 | Goshen | | A61B 6/5205 382/131 |
| 2014/0254757 A1* | 9/2014 | Oh | | A61B 6/4241 378/62 |
| 2014/0270064 A1* | 9/2014 | Oh | | A61B 6/484 378/53 |
| 2015/0036795 A1* | 2/2015 | Roessl | | A61B 6/484 378/36 |
| 2015/0049860 A1* | 2/2015 | Das | | A61B 6/4035 378/62 |
| 2015/0103970 A1* | 4/2015 | Chen | | A61B 6/484 378/5 |
| 2015/0117595 A1* | 4/2015 | Flohr | | A61B 6/4007 378/5 |
| 2015/0131777 A1* | 5/2015 | Makifuchi | | A61B 6/463 378/36 |
| 2016/0379353 A1* | 12/2016 | Makifuchi | | A61B 6/5211 382/131 |
| 2018/0120241 A1* | 5/2018 | Seetho | | G06T 11/005 |

FOREIGN PATENT DOCUMENTS

| | | | | |
|---|---|---|---|---|
| WO | WO-2015014677 A1 * | 2/2015 | | A61B 6/461 |
| WO | 2015043870 | 4/2015 | | |
| WO | 2016008956 | 1/2016 | | |
| WO | 2016023751 | 2/2016 | | |

* cited by examiner

APPARATUS FOR GENERATING MULTI ENERGY DATA FROM PHASE CONTRAST IMAGING DATA

CROSS REFERENCE TO RELATED APPLICATIONS

This application is the U.S. National Phase application under 35 U.S.C. § 371 of International Application No. PCT/EP2017/078709 filed Nov. 9, 2017, published as WO 2018/091344 on May 24, 2018, which claims the benefit of European Patent Application Number 16199050.2 filed Nov. 16, 2016. These applications are hereby incorporated by reference herein.

FIELD OF THE INVENTION

The present invention relates to an apparatus for generating multi energy data from phase contrast imaging data, to a system for generating multi energy data from phase contrast imaging data, to a method for generating multi energy data from phase contrast imaging data, as well as to a computer program element and a computer readable medium.

BACKGROUND OF THE INVENTION

The general background of this invention is the field of X-ray spectral computed tomography (CT). In a CT system an X-ray source emits X-ray radiation. The emitted radiation traverses an examination region with a subject or object located within and is detected by a detector array opposite the X-ray source. The detector array detects the radiation traversing the examination region and the subject and generates projection data, e.g. raw detector data or projection images. A reconstructor processes the projection data and reconstructs a volumetric image of the subject or object. X-ray Spectral CT is an imaging modality that extends the capabilities of a conventional CT system. Dual-Energy (DE) CT, which is a specific configuration of spectral CT, utilizes two attenuation values acquired at two photon energies to solve the photoelectric and Compton contribution that consists of the mass attenuation coefficient of a material, and thus to identify an unknown material by its value of photoelectric and Compton contribution. This scheme works especially well in materials such as iodine that has k-edge energy close to the mean value of a diagnostic energy range. Because any two linearly independent sums of two basis functions span the entire attenuation coefficient space, any material can be represented by a linear combination of two other materials, so called basis materials, such as water and iodine. The basis material images provide new applications such as monochromatic image, material cancellation image, effective atomic number image and electron density image. There are several approaches to perform dual energy CT acquisition such as dual-source, fast kVp switching, and dual-layer detector configurations. In addition, quantitative imaging is one of the current major trends in the medical imaging community. Spectral CT supports this trend, as the additional spectral information improves the quantitative information that can be measured about the scanned object and its material composition.

However, such X-ray spectral data may not be directly accessible, and/or the noise levels in the resultant Compton and photoelectric basis data sets may need to be improved, and/or there may be a need to provide augmented Dual Energy data such as multi energy data, for example providing for the visualization of an image as three separate different material images.

US2015/0103970A1 describes systems and methods for generating x-ray phase contrast images from conventional x-ray attenuation data. X-ray attenuation coefficients generated over a range of x-ray energies are used to compute the x-ray phase signal up to a calibration constant. This calibration constant is computed from provided calibration data, which may be obtained using a dedicated x-ray differential phase contrast imaging system to measure the decrement of the refractive index of a calibration phantom.

SUMMARY OF THE INVENTION

It would be advantageous to have improved apparatus for generating multi energy data.

The object of the present invention is solved with the subject matter of the independent claims, wherein further embodiments are incorporated in the dependent claims. It should be noted that the following described aspects and examples of the invention apply also to the apparatus for generating multi energy data from phase contrast imaging data, the system for generating multi energy data from phase contrast imaging data, the method for generating multi energy data from phase contrast imaging data and for the computer program element and the computer readable medium.

In a first aspect, there is provided an apparatus for generating multi energy data from phase contrast imaging data, comprising:
an input unit; and
a processing unit.

The input unit is configured to provide the processing unit with phase contrast X-ray image data of a region of interest of an object. The input unit is also configured to provide the processing unit with attenuation X-ray image data of the region of interest of the object. The processing unit is configured to generate multi energy data comprising two basis data sets. The processing unit is configured to generate a first basis data set from the phase contrast X-ray image data. The processing unit is also configured to generate a second basis data set from the phase contrast X-ray image data and the attenuation X-ray image data.

In other words, phase contrast imaging data of an object, acquired for example by a Differential Phase Contrast Imaging (DPCI) system, can be used with attenuation image data of the same object to provide two basis sets of multi energy data for that object. The two basis sets could be data such as Compton data and Photoelectric data, or data sets for two materials such as water and iodine. The basis sets, Compton, Photoelectric, Water, Iodine, can be considered to be "base materials" and do not need to relate to real materials, but can also be considered to be virtual materials. However, the region of interest of the object can then be represented in the multi energy domain, for example being represented as two images one of water and one or iodine, or one of Compton scatter and one of Photoelectric attenuation etc. This multi energy data for that object that could previously only be generated on the basis of spectrally resolved image data that was then decomposed into a Compton scattering image and a Photoelectric attenuation image, or other basis material set such as water and iodine.

To put this another way, multi energy information is obtained from a phase contrast image.

In this manner, Dual Energy (DE) or Multi-Energy (ME) information can be generated from a DPCI acquisition.

In this way, the attenuation image can be non energy sensitive, but in combination with phase contrast data multi energy data can be generated. However, if the attenuation data does relate to an energy sensitive acquisition, such as that acquired with a spectrally resolved DE or ME measurement or acquisition, then the phase contrast image data can be used to enrich the material decomposition of the DE or ME data with the Compton scattering absorption data obtained from (or using) the phase contrast data, and similarly to enrich other basis sets such as Water and Iodine. This leads to an improvement in the noise of the Compton scattering data and an improvement in the noise of the photoelectric data. Furthermore, having the phase contrast data and the multi energy attenuation data enables the generation of a basis set of three base materials, where the attenuation data can normally only be used to generated a two base material basis set.

Thus, previously acquired data can be processed to provide multi energy data, through utilisation of phase contrast data, or that multi energy data could be generated in real time from data that is being acquired from an appropriate acquisition system, and that is then being processed.

In an example, the first basis data set comprises Compton data. The Compton data corresponds to Compton scattering total attenuation coefficient data. The second basis data set can then comprise Photoelectric data. The Photoelectric data corresponds to Photoelectric total attenuation coefficient data.

In other words, phase contrast imaging data of an object, acquired for example by a Differential Phase Contrast Imaging (DPCI) system, can be used with attenuation image data of the same object to provide Compton data and Photoelectric data for that object that could previously only be generated on the basis of spectrally resolved image data that was then decomposed into a Compton scattering image and a Photoelectric attenuation image.

To put this another way, multi energy information is obtained from a phase contrast image.

When the attenuation image is a spectrally resolved DE or ME measurement or acquisition, then the phase contrast image data can be used to enrich the material decomposition of the DE or ME data with the Compton scattering absorption data obtained from (or using) the phase contrast data. This leads to an improvement in the noise of the Compton scattering data and an improvement in the noise of the photoelectric attenuation data.

In an example, the processing unit generates the first basis data set from the phase contrast X-ray image data on the basis that phase contrast X-ray image data at an image location is proportional to first basis data at that image location.

In the first aspect, generation of the second basis data set comprises utilisation of the first basis data set.

In other words, having calculated the first basis data set, the first data set with the total attenuation can be used to calculate the second basis data set.

In an example, a spectral detector sensitivity of a detector used to acquire the phase contrast X-ray image data is the same as a spectral detector sensitivity of a detector used to acquire the attenuation X-ray image data. A baseline intensity signal then relates to a detected signal on the detector when the object is not present. In this example, a spectrum of an X-ray source used during the acquisition of the phase contrast X-ray image data is the same as a spectrum of an X-ray source used during the acquisition of the attenuation X-ray image data. Generation of the second basis data set then comprises utilisation of the spectral detector sensitivity of the detector and the baseline intensity signal and the spectrum of the X-ray source.

In other words, information normally used in material decomposition of DE or ME data is used in an inverse way to determine the second basis data set.

Thus, it need not be the same detector and X-ray source pair that is used to acquire the phase contrast data that is used to acquire the attenuation data, so long as the spectral sensitivities of the detectors are known and the spectrums of the X-ray sources are known.

In an example, generation of the second basis data set comprises utilisation of an energy dependence relating to data of the first basis data set and an energy dependence relating to data of the second basis data set.

In an example, the detector used to acquire the phase contrast X-ray image data is the same as the detector used to acquire the attenuation X-ray image data. In this example, the X-ray source used during the acquisition of the phase contrast X-ray image data is the same as the X-ray source used during the acquisition of the attenuation X-ray image data.

Thus, the same detector and X-ray source pair that is used to acquire the phase contrast data is the same as that is used to acquire the attenuation data.

In an example the attenuation X-ray image data comprises spectral image data.

In this way, material decomposition of the DE or ME data to generate basis sets, such as Compton scatter and photoelectric images, can be enriched with the Compton scatter data acquired using the phase contrast image data.

Thus, a basis material set of three "base materials" can be generated, rather than a generation of two base materials as can normally be done from spectral attenuation data. This is enabled through the use of the phase contrast data.

In an example, the processing unit is configured to decompose the spectral image data into at least one basis image, the at least one basis image comprising a first basis data set image.

In an example, the phase contrast X-ray image data and the attenuation X-ray image data were acquired at the same time.

In other words, the transmitted beam that passes through an object that is interrogated to produce a phase contrast image, can at the same time be used to produce an attenuation image. And, these phase contrast and attenuation data can be processed to generated multi energy information.

In this manner, there is a direct correspondence between the attenuation image and the phase contrast image, thereby facilitating the generation of the second basis data set from the phase contrast data and the attenuation data, (such as generating the Photoelectric data from the phase contrast data and the attenuation data).

In an example, the processing unit is configured to generate multi energy and/or dual energy information on the basis of the first basis data set and second basis data set. The information can comprise at least one image of the region of interest of the object.

In other words, the phase contrast image data, along with attenuation image data, can be used to provide basis set imagery (such as a Compton scattering image and a Photoelectric attenuation image, or an image of one material and an image of a second material for example), that would normally be required to be generated using spectrally resolved data acquisition and decomposition of that spectrally resolved data. But now, this equivalent data can be generated from an attenuation image and a phase contrast image.

In a second aspect, there is provided a system for generating multi energy data from phase contrast imaging data, the system comprising:

at least one image acquisition unit;
an apparatus for generating multi energy data from phase contrast imaging data according to the first aspect; and
an output unit.

The at least one image acquisition unit is configured to acquire the phase contrast X-ray image and to acquire the attenuation X-ray image. The output unit is configured to output multi energy and/or dual energy information on the basis of the first basis data set and the second basis data set.

In a third aspect, there is provided a method for generating multi energy data from phase contrast imaging data, comprising:
a) providing phase contrast X-ray image data of a region of interest of an object;
b) providing attenuation X-ray image data of the region of interest of the object;
c) generating a first basis data set from the phase contrast X-ray image data; and
d) generating a second basis data set from the phase contrast X-ray image data and the attenuation X-ray image data.

According to another aspect, there is provided a computer program element controlling apparatus as previously described which, when the computer program element is executed by a processing unit, is adapted to perform the method steps as previously described.

According to another aspect, there is provided a computer readable medium having stored computer element as previously described.

Advantageously, the benefits provided by any of the above aspects equally apply to all of the other aspects and vice versa.

The above aspects and examples will become apparent from and be elucidated with reference to the embodiments described hereinafter.

BRIEF DESCRIPTION OF THE DRAWINGS

Exemplary embodiments will be described in the following with reference to the following drawings.

DETAILED DESCRIPTION OF EMBODIMENTS

Figure 1:
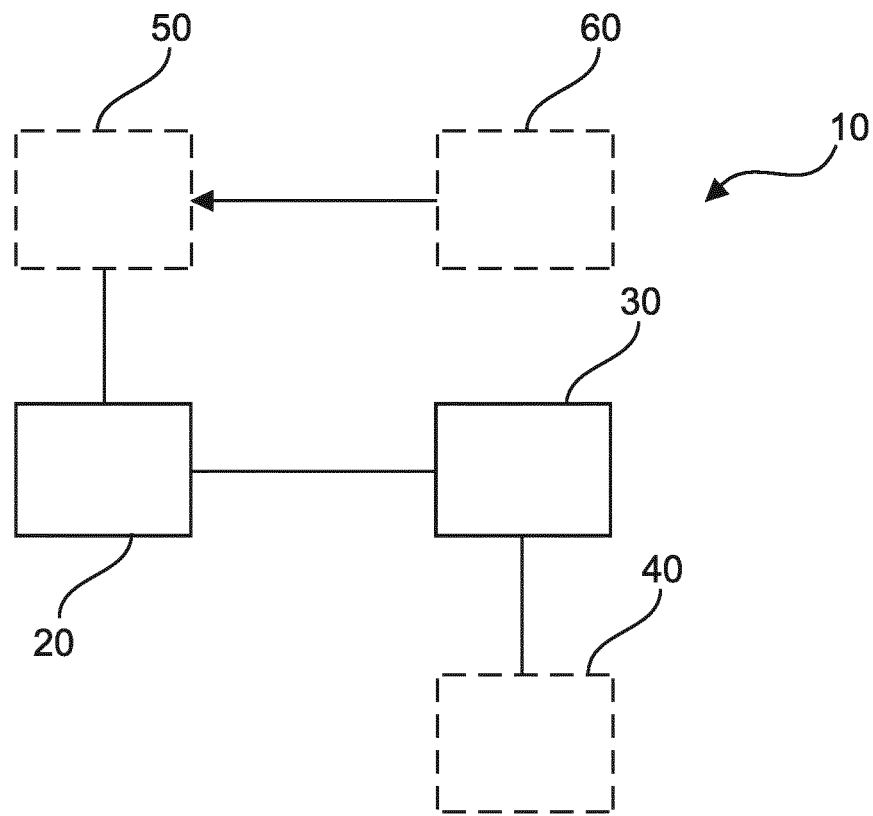
FIG. 1 shows a schematic set up of an example of an apparatus for generating multi energy data from phase contrast imaging data.

FIG. 1 shows an example of an apparatus 10 for generating multi energy data from phase contrast imaging data. The apparatus 10 comprises an input unit 20, and a processing unit 30. The input unit 20 is configured to provide the processing unit 30 with phase contrast X-ray image data of a region of interest of an object, via wired or wireless communication. The input unit 20 is configured also to provide the processing unit 30 with attenuation X-ray image data of the region of interest of the object, again via wired or wireless communication. The processing unit 30 is configured to generate multi energy data comprising two basis data sets. To do this, the processing unit 30 is configured to generate a first basis data set from the phase contrast X-ray image data. The processing unit 30 is also configured to generate a second basis data set from the phase contrast X-ray image data and the attenuation X-ray image data.

In an example, the X-ray attenuation image is a radiography image.

In an example, the X-ray attenuation image is an angiographic image.

In an example wherein the processing unit is configured to register phase contrast X-ray image data to the attenuation X-ray image data. By registering the phase contrast X-ray image data to the attenuation X-ray image data image, phase contrast images and attenuation images of the body part acquired at different times, and even by different acquisition systems, can be analysed efficiently enabling a region in the phase contrast image to be matched to an equivalent region in the attenuation image. This facilitates the generation of the Photoelectric data from the phase contrast data (or other base material set) and the attenuation data.

In an example, registering accounts for the patient's cardiac cycle and/or breathing cycle.

In an example, registering may comprise the step of warping the region of interest of an attenuation image and/or the region of interest of a phase contrast image.

In an example, acquisition of the attenuation image data is performed at the same angulation as that used for acquisition of the phase contrast image data. For example, both acquisitions are performed with the same C-arm angulation. This provides for ease of aligning the images.

In an example, the aligning leads to a spatial matching of the region of interest of an attenuation image with the region of interest of a phase contrast image.

In an example, registering a phase contrast image to an attenuation X-ray image comprises application of a segmentation procedure.

In an example, the processing unit is configured to determine a location in an X-ray attenuation image on the basis of an equivalent location in a phase contrast X-ray image. This helps to facilitate the generation of the second basis data set (e.g. Photoelectric data) from the phase contrast data and the attenuation data. In an example, the locating comprises application of a segmentation procedure.

In an example, apparatus comprises an output unit 40. The output unit 40 is configured to output multi energy and/or dual energy information on the basis of the first basis data set and the second basis data set (e.g. Compton data and the Photoelectric data).

According to an example, the first basis data set comprises Compton data, the Compton data corresponding to Compton scattering total attenuation coefficient data. The second basis data set can then comprise Photoelectric data, the Photoelectric data corresponding to Photoelectric total attenuation coefficient data.

According to an example, the processing unit 30 is configured to generate the first basis data set from the phase contrast X-ray image data on the basis that phase contrast X-ray image data at an image location is proportional to first basis data at that image location.

In an example, the processing unit 30 is configured to generate the Compton data from the phase contrast X-ray image data on the basis that phase contrast X-ray image data at an image location is proportional to Compton scattering total attenuation coefficient data at that image location.

In other words, knowledge is used that the phase contrast signature is proportional to the electron density which is proportional to the Compton scatter.

According to an example, generation of the second basis data set comprises utilisation of the first basis data set.

In an example, generation of the Photoelectric data comprises utilisation of the Compton data.

In other words, with the total attenuation and the Compton scatter absorption the photoelectric absorption can be calculated.

According to an example, a spectral detector sensitivity of a detector 50 used to acquire the phase contrast X-ray image data is the same as a spectral detector sensitivity of a detector 50 used to acquire the attenuation X-ray image data. A baseline intensity signal can then be determined or defined, that relates to a detected signal on or from the detector(s) 50 when the object is not present. In this example, a spectrum of an X-ray source 60 used during the acquisition of the phase contrast X-ray image data is the same as a spectrum of an X-ray source 60 used during the acquisition of the attenuation X-ray image data. Generation of the second basis data set then comprises utilisation of the spectral detector sensitivity of the detector(s) 50 and the baseline intensity signal and the spectrum of the X-ray source(s) 60. Here, there could be just one detector 50, or two detectors 50, and there could be two X-ray sources 60 or just one X-ray source 60.

In an example, generation of the Photoelectric data comprises utilisation of the spectral detector sensitivity of the detector and the baseline intensity signal and the spectrum of the X-ray source.

In other words, information normally used in material decomposition of DE or ME data is used in an inverse way to determine the Photoelectric absorption.

According to an example, generation of the second basis data set comprises utilisation of an energy dependence relating to data of the first basis data set and an energy dependence relating to data of the second basis data set.

In an example, generation of the Photoelectric data comprises utilisation of an energy dependence of the Compton scattering effect and an energy dependence of the Photoelectric attenuation effect.

According to an example, the detector 50 used to acquire the phase contrast X-ray image data is the same as the detector 50 used to acquire the attenuation X-ray image data. In an example, the X-ray source 60 used during the acquisition of the phase contrast X-ray image data is the same as the X-ray source 60 used during the acquisition of the attenuation X-ray image data.

According to an example, the attenuation X-ray image data comprises spectral image data.

In an example, the spectral image data comprises DE or ME image data. In an example, the spectral image data is acquired with a spectrally resolving detector, such as a dual layer detector array.

According to an example, the processing unit 30 is configured to decompose the spectral image data into at least one basis image. The at least one basis image can then comprise a first basis data set image.

In an example, the processing unit 30 is configured to decompose the spectral image data into at least one basis image, and the at least one basis image can comprises a second basis data set image.

In an example, the processing unit 30 is configured to decompose the spectral image data into at least one basis image, and the at least one basis image can comprise a Compton attenuation coefficient image.

In an example, the processing unit is configured to decompose the spectral image data into a Compton attenuation coefficient image and a Photoelectric attenuation coefficient image.

According to an example, the phase contrast X-ray image data and the attenuation X-ray image data were acquired at the same time.

According to an example, the processing unit is configured to generate multi energy and/or dual energy information on the basis of the first basis data set and second basis data set. The multi energy and/or dual energy information can then comprise at least one image of the region of interest of the object.

In an example, the processing unit is configured to generate multi energy and/or dual energy information on the basis of the Compton data and Photoelectric data. The multi energy and/or dual energy information can comprise at least one image of the region of interest of the object.

Figure 2:
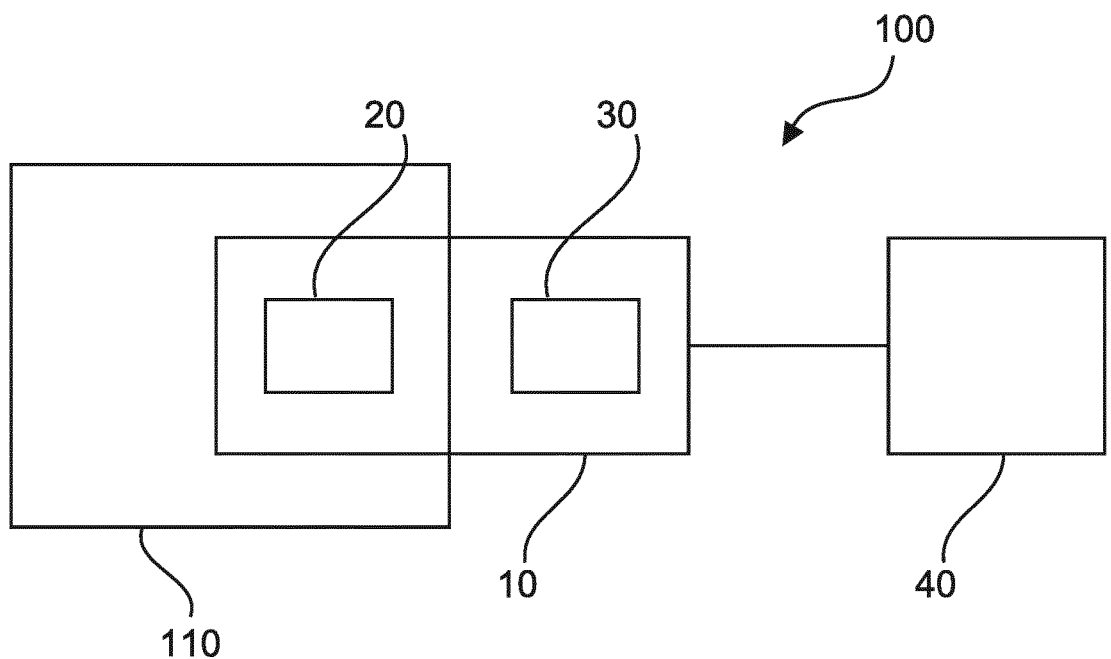
FIG. 2 shows a schematic set up of an example of a system for generating multi energy data from phase contrast imaging data.

FIG. 2 shows an example of a system 100 for generating multi energy data from phase contrast imaging data. The system 100 comprises at least one image acquisition unit 110, and an apparatus 10 for generating multi energy data from phase contrast imaging data as described with respect to FIG. 1. The system 100 also comprises an output unit 120. The at least one image acquisition unit 110 is configured to acquire the phase contrast X-ray image and to acquire the attenuation X-ray image. The output unit 120 is configured to output multi energy and/or dual energy information on the basis of the first basis data set and the second basis data set.

In an example, the at least one image acquisition unit 120 provides the phase contrast X-ray image and the attenuation X-ray image to the input unit 20 via wired or wired communication. In an example, the at least one image acquisition unit 120 is the input unit 20. In an example, an image acquisition unit of the at least one image acquisition unit 120 is the input unit 20.

In an example, the output unit is configured to output multi energy and/or dual energy information on the basis of the Compton data and the Photoelectric data.

In an example, the at least one image acquisition unit comprises a grating based differential phase contrast imaging device. In an example, the at least one image acquisition unit comprises a grating based differential phase contrast and dark field X-ray imaging device. In an example, the at least one image acquisition unit comprises an interferometer arrangement.

In an example, the at least one image acquisition unit comprises an X-ray imaging device. For example, the device can be a tomography arrangement, or a CT arrangement.

In an example, the at least one image acquisition unit can operate in a standard radiography mode, with transmitted intensities of radiation providing information on attenuation through the object. In an example, the at least one image acquisition unit can operate in a Differential phase contrast imaging (DPCI) mode. In an example, the same image acquisition unit can be used to acquire the attenuation and phase contrast images. In an example, the same image acquisition unit can be used to acquire the attenuation and dark field and phase contrast images. For example, an interferometer arrangement of a DPCI apparatus can be swung out of the X-ray beam and a normal radiography, attenuation, image acquired. Then, the interferometer arrangement can be swung back into the X-ray beam and the dark field X-ray or phase contrast image acquired.

In an example, the at least one image acquisition unit comprises a differential phase contrast imaging (DPCI) apparatus. In an example, the at least one image acquisition unit generates an attenuation image, relating to the detection of intensity (intensity) values of X-rays with and without the object in the examination region. In an example, the at least one image acquisition unit generates a phase contrast (or differential phase) image, relating to the detection of the phases of the X-rays with and without the object in the examination region. In an example, the at least one image acquisition unit generates a dark field (or de-coherence) image, relating to the detection of fringe visibilities of the X-rays with and without the object in the examination region. In an example, the at least one image acquisition unit generates any combination of these images. For example, the at least one image acquisition unit can generate an attenuation image, and generate a phase contrast image, and generate a dark field image. In an example, an attenuation image and a phase contrast image can be generated at the same time. In an example, an attenuation image, a phase contrast image, and a dark field image can be generated at the same time.

In an example, the interferometer arrangement comprises a Talbot interferometer. In an example, the interferometer arrangement comprises a diffraction grating configured to modulate onto the X-rays emitted by the source an interference pattern detectable by the X-ray detector as X-ray fringes. In an example, the interferometer arrangement comprises a second diffraction grating configured to analyze the interference pattern. In an example, the second diffraction grating is an absorption grating. In an example, the two gratings are arranged on mutually opposite sides of an examination region. In an example, the two gratings are arranged on the same side of an examination region. In an example, the interferometer comprises a source grating in addition to the one or two gratings already discussed. In this example, the source grating is located relatively close to the X-ray source and serves to make the X-rays propagating after the source grating partly coherent. In other words, an X-ray source can be adapted so as to emit radiation that is more coherent than if the source grating was not present. Therefore, in some examples a source grating is not required, for example when the X-ray source already produces suitably coherent X-rays. In an example, the interferometer arrangement is configured to produce Moiré fringes. In an example, the interferometer arrangement is purposely detuned such that some fringes are present in a detector area. In an example, the interferometer arrangement is purposely detuned by having a first grating inclined at a small angle to a second grating. In an example, detuning leads to the generation of Moiré fringes on the detector.

In one example, the interferometer arrangement comprises two gratings which are fixedly mounted with respect to each other in a suitable frame or cage and this frame is fixedly arranged in a scan arm or other moveable gantry structure. In other words, the interferometer arrangement can be swung in and out of the X-ray beam such that the apparatus can be operated in both a DPCI mode and in a conventional radiography mode. In the DPCI mode, the arm can be translated or rotated, such that at least part of the object is scanned.

In an example, the output unit outputs an absorption (or attenuation) image. In an example, the output unit outputs a phase contrast (or differential phase) image. In an example, the output unit outputs a dark field image. In an example, the output unit outputs any combination of attenuation, phase contrast and dark field images. In other words, the output unit can simultaneously output the attenuation image and the phase contrast image and in another example can simultaneously output all three types of image. In an example, the output unit outputs data representative of the object on a monitor such as a visual display unit or on a number of separate monitors. For example, attenuation, phase contrast and dark field images can be presented on a single monitor or presented on separate monitors.

In an example, the output unit outputs the Compton data and the Photoelectric data. In an example, the output unit outputs an image represented by Compton data. In an example, the output unit outputs an image represented by photoelectric data. In other words, phase contrast imaging data and attenuation imaging data can be utilised to generate equivalent basis set imagery that is normally acquired from multi-energy spectrally resolving systems, where such data from multi-energy spectrally resolved system is decomposed into for example a Compton scattering image and a photoelectric attenuation image. However, here a phase contrast image and an attenuation image, which could be acquired at the same time in a DPCI system, are used to generate equivalent Compton scattering and photoelectric attenuation images (or other basis set data or imagery).

In an example, the system has useful application in a clinical environment such as a hospital. In an example, the system can be used for mammography, diagnostic radiology and interventional radiology for the medical examination of patients. In an example, the system has useful application in an industrial environment, for example in non-destructive testing (e.g. analysis as to composition, structure and/or qualities of biological as well non-biological samples) as well as security scanning (e.g. scanning of luggage in airports). The apparatus has this application applicability too, as well as the method discussed below.

In an example, the fringe pattern generated at a current scan arm position is used to determine a visibility or mean visibility and at the same time is used to determine a transmission intensity of X-ray radiation at that arm position. In other words, an attenuation image can be acquired at the same time as a phase contrast image, and also if necessary a dark field image can be acquired at the same time.

In an example, an image acquisition unit, such as a C-arm system, is used to acquire the attenuation image, and a different image acquisition unit, such as a DPCI system, is used to acquire the phase contrast image. In an example, an image acquisition unit, such as a C-arm system, is used to acquire the attenuation image, and a different image acquisition unit, such as a DPCI system, is used to acquire the phase contrast image. The DPCI system can also acquire a dark field image if necessary.

In an example, the object is a body or body part. In an example, the object is a piece of luggage or a part of a piece of luggage or a piece of luggage and its contents. In an example, the object is a part of an industrial device or machine part.

Figure 3:
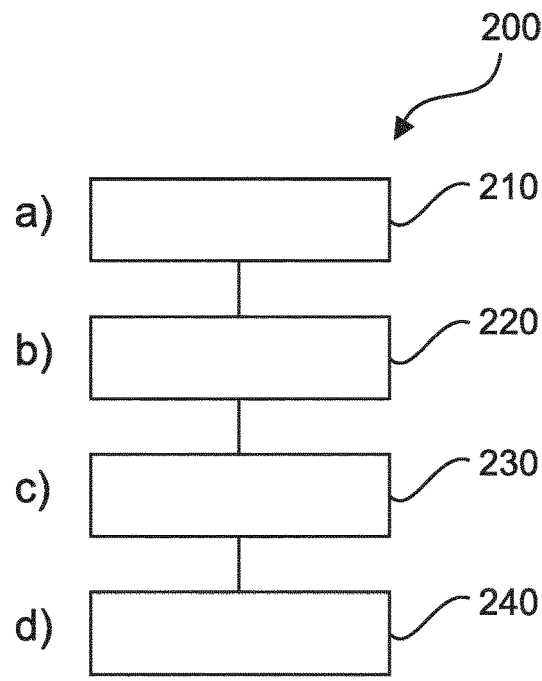
FIG. 3 shows a method for generating multi energy data from phase contrast imaging data.

FIG. 3 shows a method 200 for generating multi energy data from phase contrast imaging data in its basic steps. The method 200 comprises:

in a providing step 210, also referred to as step a), providing phase contrast X-ray image data of a region of interest of an object;

in a providing step 220, also referred to as step b), providing attenuation X-ray image data of the region of interest of the object;

in a generating step 230, also referred to as step c), generating a first basis data set from the phase contrast X-ray image data; and In a generating step 240, also referred to as step d), generating a second basis data set from the phase contrast X-ray image data and the attenuation X-ray image data, and wherein step d) comprises utilizing the first basis data set.

In an example, step c) comprises generating Compton data from the phase contrast X-ray image data, the Compton data corresponding to Compton scattering total attenuation coefficient data.

In an example, step d) comprises generating Photoelectric data from the phase contrast X-ray image data and the attenuation X-ray image data, the Photoelectric data corresponding to Photoelectric total attenuation coefficient data.

In an example, in step a) an input unit 20 provides the phase contrast X-ray image data to a processing unit 30.

In an example, in step b) the input unit provides the attenuation X-ray image data to the processing unit.

In an example, in step c) the generating is carried out by the processing unit.

In an example, in step d) the generating is carried out by the processing unit.

In an example, step c) comprises generating the first basis data set on the basis that phase contrast X-ray image data at an image location is proportional to data of the first basis data set at that image location.

In an example, step c) comprises generating the Compton data on the basis that phase contrast X-ray image data at an image location is proportional to Compton scattering total attenuation coefficient data at that image location.

In an example, step d) comprises utilising the first basis data set.

In an example, step d) comprises utilising the Compton data.

In an example, a spectral detector sensitivity of a detector used to acquire the phase contrast X-ray image data is the same as a spectral detector sensitivity of a detector used to acquire the attenuation X-ray image data; and a baseline intensity signal relates to a detected signal on the detector when the object is not present; and a spectrum of an X-ray source used during the acquisition of the phase contrast X-ray image data is the same as a spectrum of an X-ray source used during the acquisition of the attenuation X-ray image data; and step d) then comprises utilising the spectral detector sensitivity of the detector and the baseline intensity signal and the spectrum of the X-ray source.

In an example, step d) comprises utilising an energy dependence relating to data of the first basis data set and an energy dependence relating to data of the second basis data set.

In an example, step d) comprises utilising an energy dependence of the Compton scattering effect and an energy dependence of the Photoelectric attenuation effect.

In an example, the detector used to acquire the phase contrast X-ray image data is the same as the detector used to acquire the attenuation X-ray image data; and the X-ray source used during the acquisition of the phase contrast X-ray image data is the same as the X-ray source used during the acquisition of the attenuation X-ray image data.

In an example, the attenuation X-ray image data comprises spectral image data.

In an example, the method comprises decomposing the spectral image data into at least one basis image, the at least one basis image comprising a first basis data set image.

In an example, the method comprises decomposing the spectral image data into at least one basis image, the at least one basis image comprising a second basis data set image.

In an example, the method comprises decomposing the spectral image data into at least one basis image, the at least one basis image comprising a Compton attenuation coefficient image.

In an example, the method comprises decomposing the spectral image data into at least one basis image, the at least one basis image comprising a Photoelectric attenuation coefficient image.

In an example, the phase contrast X-ray image data and the attenuation X-ray image data were acquired at the same time.

The following detailed example is discussed in relation to Compton scatter and photoelectric effect, however as discussed above there is general applicability to other base material sets.

Differential Phase Contrast Imaging (DPCI) is a new imaging method that uses a set of gratings to obtain phase contrast information from an X-Ray imaging setup such as projection imager or CT. The grating set-up is discussed in more detail below. The DPCI method generates typically three images simultaneously. Beside the so-called dark field image a conventional attenuation image and a phase contrast image is generated. The phase contrast image is proportional to the local electron density of the object.

Dual (DE) and Multi energy imaging (ME) for radiography or CT uses multiple imaging channels with different spectral coding. The information of these channels is typically processed with a material decomposition method to obtain material specific information of the scanned object. In DE the data can be decomposed into the contribution made by the Compton scatter and photoelectric effects relating to the total attenuation. These two bases can later be used to generate other material images. The additional spectral information obtained in ME allows for advanced decomposition and can be used to do K-edge imaging.

In other words, as discussed above the presently described apparatus, system and method enables the generation of DE or ME information from a DPC acquisition.

With the attenuation and phase contrast projection data of an object the Compton effect and photoelectric absorption can be calculated. The phase contrast signature is proportional to the electron density which is proportional to the Compton scatter. With the total attenuation and the Compton scatter absorption the photoelectric absorption can be calculated. The forward model used for the DE decomposition is usually:

$$I=I^0\int dR \cdot R(E) \cdot D(E) e^{-A_0 f_0(E) - A_1 f_1(E)}.$$

Where I is the expected detected X-Ray intensity signal, $I_0$ the signal without the object, $R(E)$ is the spectrum of X-Ray source, $D(E)$ is the spectral detector sensitivity, $A_0$ and $A_1$ are the contributions of Compton scatter and the photoelectric absorption and $f_0$ and $f_1$ being the energy dependence of the two effects. The imaging device parameter $I_0$, $R(E)$, $D(E)$ can be determined or are readily known, as would be appreciated by the skilled person. As stated above, the phase contrast is proportional to the Compton scatter $A_0=wP$ with factor w. Depending on the imaging system, we can either directly extract the intensity I from the measurements or we can calculate it. Now we have all parameters from the forward model except $A_1$ which can now be calculated.

As discussed above, dual energy data can be provided from the phase contrast data in combination with attenuation data. However, if the attenuation data itself has spectral content, i.e. if an energy sensitive (DE or ME) measurement is performed, the same idea can be used to enrich the material decomposition with the known Compton scatter absorption obtained from the phase contrast data. In case the total number of energy channels plus one is larger than the amount of base materials in the decomposition, a statistical decomposition technique can be used to improve the noise performance.

In general terms the multi energy system model with $n=1 \ldots N$ spectral channels is a set of N equations:

$$I_n = I_n^0 \int dE \cdot R_n(E) \cdot D_n(E) e^{-A_0 f_0(E) - \Sigma_{m \in M} A_m f_m(E)}$$

in which a set M of base materials are used. M can exclude the Compton scatter base $A_0 f_0(E)$ which can be taken or determined from the phase contrast data. The set of base materials should include the photoelectric effect and can optionally include one or more materials with a K-edge in the acquisition spectrum such as Gold or Gadolinium. In a conventional DE or ME system there may be only n base materials including Compton scatter. If we get the Compton scatter from the phase contrast, the base materials can now include n+1 materials including Compton scatter. In other words, rather than being able to represent an imaged object as two different materials it can now be represented as three different materials, enabling better feature differentiation.

Regarding the above, the term "base materials" in this context does not necessarily refer to real materials. A material can also be a virtual material defined by its spectral absorption characteristics (e.g. photoelectric effect or Compton scatter). Real materials such as soft tissue or bone are decomposed into a set of virtual photoelectric effect and Compton materials with the identical combined absorption.

Thus to summarize, the technique can be used to obtain Dual energy information from a none energy selective phase contrast measurement or it can be used to replace the Compton effect base in a multi energy phase contrast system model with the phase contrast. In both of these, the spectral decomposition can be enabled or improved with an additional information channel.

Different elements of the apparatus, system and method for generating multi energy data from phase contrast imaging data will now be described in more detail in conjunction with FIGS. 4-7.

Figure 4:
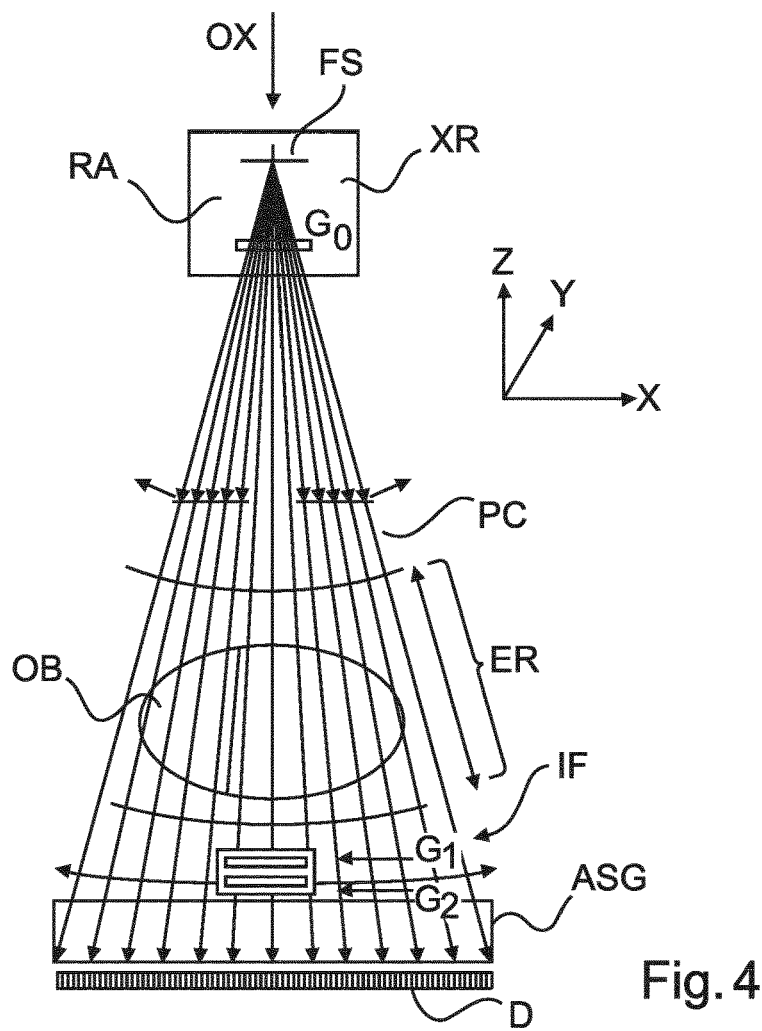
FIGS. 4-5 shows schematic set ups of examples of a system for generating multi energy data from phase contrast imaging data.

FIG. 4 shows an example of system 100 for generating multi energy data from phase contrast imaging data The system 100 can for acquire the X-ray dark field and/or phase contrast images and can also acquire X-ray attenuation images. The system is capable of imaging for the spatial distribution of absorption of, or in, an object OB and also capable of imaging for the spatial distribution of refraction (phase contrast imaging) and also capable of imaging for the spatial distribution of small angle scattering (dark field imaging). The apparatus has a grating based interferometer IF that can be scanned across a stationary X-ray detector D 50. In this example, the interferometer IF comprises two grating structures G1 and G2 although, although in other examples a single grating interferometer (having only a single grating G1) is used. In the specific case of a single grating interferometer IF, the X-ray detector D has a pitch sufficiently small, hence a spatial resolution sufficiently large, for detecting i.e. adequately resolving the interference pattern generated by the grating G1 for the purpose of differential phase contrast imaging and/or dark field imaging. For that purpose the X-ray detector may be a high resolution X-ray detector, having for example a spatial resolution of 50 micrometers or more.

In FIG. 4, the grating G1 is either an absorption grating or phase shift grating whereas G2 is an absorption gating. The gratings are manufactured by photo lithographically processing suitable substrates such as a silicon wafer. A pattern of periodic rulings is formed in those silicon "cards" formed by trenches of different aspect ratio. The ruling patterns may be one dimensional but may also be two dimensional such as to confer a checker board pattern.

The X-ray imaging apparatus further comprises an X-ray source XR 60 and the X-ray detector D 50. The X-ray detector D can be a 2D full view X-ray detector, which is either planar or curved. A plurality of detector pixels are arranged in rows and columns as an array to form a 2D X-ray radiation sensitive surface capable of registering X-ray radiation emitted by the X-ray source.

The X-ray detector D and the X-ray source are spaced apart to form an examination region ER. The examination region is suitably spaced to receive the object OB to be imaged. The object may be inanimate or animate. For instance the object may be a piece of luggage or other sample to be imaged, or in a medical context the object may be a human or animal patient or at least an anatomic part of a human or animal.

The interferometric grating structures G1 and G2 are arranged in the examination region ER between the X-ray source XR and X-ray detector D. The X-ray source XR has a focal spot FS from which the X-ray radiation beam emerges. It is the space between the focal spot FS and the X-ray detector's radiation sensitive surface where the two or three grating structures are arranged. The grating G1 is a phase grating and the grating G2 is an analyzer grating. In some embodiments, there is in addition to the interferometric gratings G1, G2 of the interferometer IF, a further grating G0 which is the source grating.

The source grating G0 is arranged in proximity of the X-ray source 60, for example at the exit window of a housing of the X-ray tube. The function of the source grating G0 is to make the emitted radiation at least partly coherent. In other words, the source grating G0 can be dispensed with if an X-ray source is used which is capable of producing coherent radiation.

In operation the at least partly coherent radiation passes through the examination region ER and interacts with the object OB. The object then modulates the attenuation, refraction, and small angle scattering information onto the radiation which can then be extracted by operation of the grating tandem G1 and G2. The gratings G1, G2 induce an interference pattern which can be detected at the X-ray detector D as fringes of a Moiré pattern. If there was no object in the examination region, there would still be an interference patter observable at the X-ray detector D, called the reference pattern which is normally captured during a calibration procedure. This comes about by especially adjusting or "detuning" the mutual spatial relationship between the two gratings G1 and G2 by inducing a slight flexure for instance so that the two gratings are not perfectly parallel. Now, if the object is positioned in the examination region and interacts with the radiation as mentioned, the Moiré pattern, which is now more appropriately called the object pattern, can be understood as a disturbed version of the reference pattern. This difference from the reference pattern can then be used to compute one or all of the three images (attenuation, phase contrast, dark field). This means that the attenuation image is acquired at the same time as the dark field and/or phase contrast image and as such the patient will be in the same state (e.g. breathing or other movement) and image registration is made more simple, enabling a location in the attenuation image to be transferred to a location in phase contrast image and vice versa. However, the grating system can be swung out of position and the system operated in a normal radiography mode in order to obtain the attenuation data. As described above, the attenuation data and the phase contrast data can be used to generate multi energy information, such as Compton scattering attenuation data and photoelectric attenuation data. As described below with respect to FIGS. 6-7, the detector can be a spectrally resolving detector rather than a spectrally non-resolving detector. In this case the spectrally resolved data can be decomposed to provide multi-energy data and the phase contrast data can be utilized in that process in order to enrich the data, and for example reduce noise in Compton scattering and photoelectric attenuation images.

Continuing with FIG. 4, to be able to acquire suitable signals from which the images can be computed, a scanning motion is performed by the grating tandem G1-G2. As a result of this motion, at each pixel of the X-ray detector D a series of intensity values are detected. For good results, the detuning of the gratings G1, G2 is such that a period of the Moiré pattern should extend for a few of its cycles (two or three) in the direction of the scan motion. For each X-ray detector pixel, the series of intensity values can then be fitted to a (sinusoidal) signal forward model, for example, in order to derive the respective contributions of refraction, absorption, and small angle scatter. This type of signal processing is done in a signal processing unit not shown in FIG. 4, but which is known to the skilled person. The X-ray detector D remains stationary for any given orientation of the optical axis OX which is shown in FIG. 4 to extend along the Z axis. In other words, the X-ray detector D is kept stationary (at least during an image acquisition operation) with respect to an arbitrary reference point in the examination region. The interferometric setup as described above is what is commonly referred to as a Talbot-Lau interferometer. The distances between G0 and G1 and between G1 and G2 must be finely tuned to fit the requirements of Talbot distance which in turn is a function of the "pitch" (that is, the spatial period of the grating rulings) of the respective grating. Moving the interferometer IF relative to the X-ray detector D may cause a slight change in fringe distribution due to fringe drift. However, the fringe drift can be compensated by relating such drift to the fringe drift as obtained with a reference scan. Such reference scan may be a blank scan performed at the installation of the X-ray imaging apparatus.

The interferometer IF can be essentially a "grating pack" with the two gratings G1 and G2 fixedly mounted with respect to each other in a suitable frame or cage and this frame is fixedly arranged in a scan arm GT or other moveable gantry structure (not shown in FIG. 4). The arm, and with it the interferometer IF performs a pendulum like motion across the X-ray detector surface. The pivot point for the scan arm motion runs through the focal spot FS of the X-ray source but does not need to. The gratings G1 and G2 of the interferometer IF are held in fixed spatial relationship with respect to each other at all times during the scan motion and remain essentially parallel, or at least in a fixed spatial relationship, to G0. Suitable tracking circuitry (not shown) correlates interferometer position with X-ray detector pixel position to timely trigger a sequence of read-out burst to make sure each pixel is supplied with the above mentioned series of measurements to correctly sample the interference pattern.

In FIG. 4, the X-Y plane is the X-ray detector plane with X,Y designating the direction of pixelation in the X-ray detector D. The X-ray source rotates around the focal point that passes through the focal spot FS. The rotation axis RA for the scan arm GT and X-ray source XR extends into the paper plane of FIG. 4 (along the Y direction). Having the X-ray source rotate in concert with the pendulum motion of the grating tandem G1, G2 allows increasing flux.

In the example of FIG. 4, a pre-collimator is arranged between the X-ray source and the object OB so as to conform the radiation beam to the dimensions or footprint of the gratings G1 and/or G2. The collimator PC moves in concert with the pendulum motion of the interferometer IF during the image acquisition. One way to achieve this is to mount the collimator to the scan arm GT proximate to the source grating G0 at an appropriate distance. The source grating G0 also moves in concert with the swinging scanning motion of the grating pack G1, G2. One way to do this is to mount the grating in the scan arm. An anti-scatter grid ASG may be arranged between the interferometer and the X-ray detector surface.

In the example of FIG. 4 it is envisaged that the object, e.g. a patient, OB lies on an examination table or couch (not shown in FIG. 14) during the image acquisition. In other words the patient's longitudinal axis extends into the drawing plane as per FIG. 14 whilst the pendulum motion of the gratings G1, G2 (and that of G0) swings in a vertical plane with the patient's longitudinal axis (in FIG. 4 extending into the Y direction) extending into the paper plane of FIG. 4.

The mutually rigidly mounted gratings G1, G2 move the full length from one X-ray detector edge to the opposing X-ray detector edge if a full field image is desired, i.e. an image that is as wide in scan direction as the X-ray detector itself. If the user requests a smaller FOV (field of view), however, a reduced scan range can be used to minimize the acquisition time.

Figure 5:
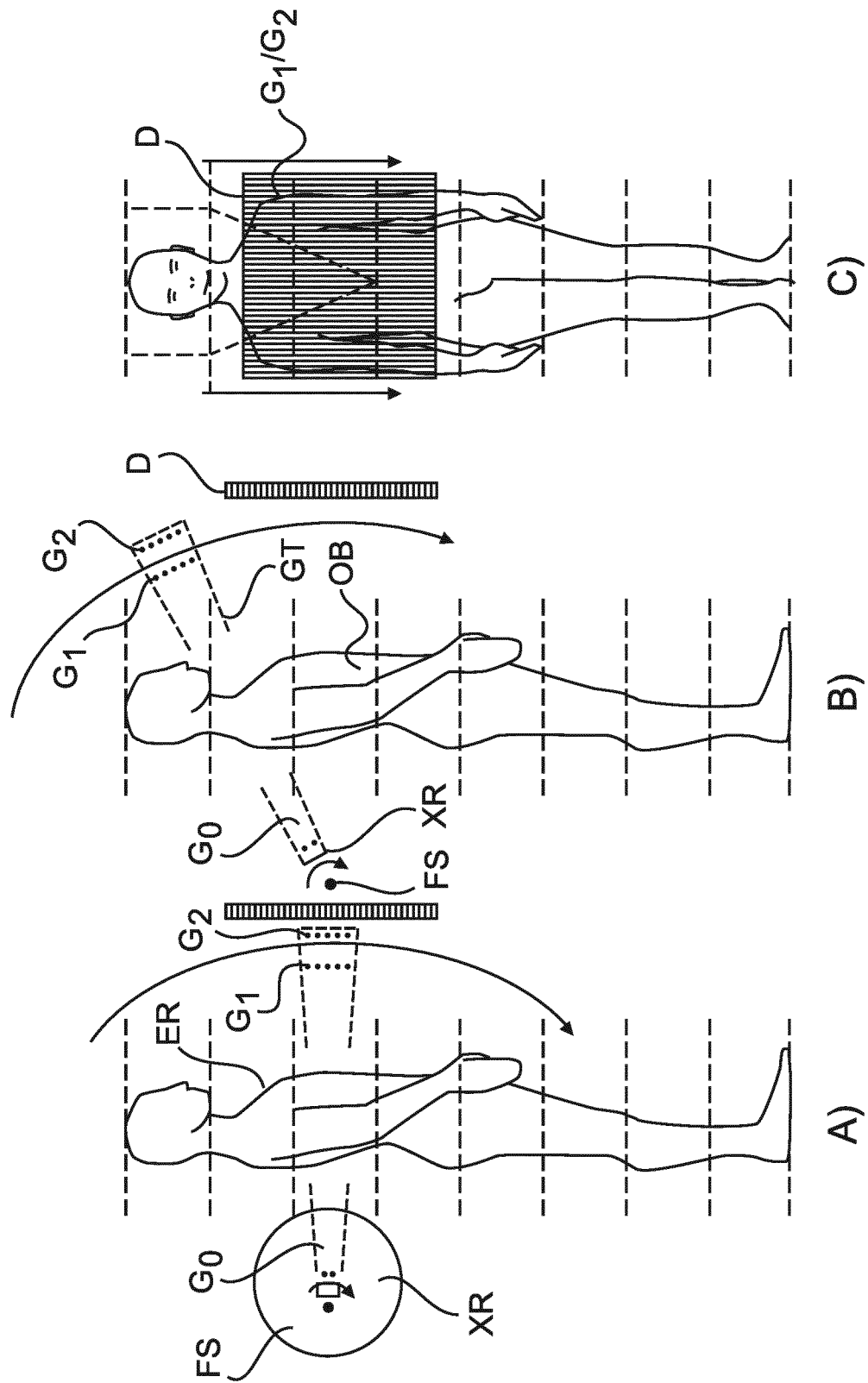

FIG. 5 shows a different example configured to allow the patient to stand (upright) during the X-ray imaging acquisition. This construction may be beneficial for chest imaging. Views A, B represent side elevations of the arrangement whilst view C is a frontal view through the X-ray detector D towards the X-ray source XR, that is, along the optical axis OX. Compared to FIG. 4 the optical axis in the FIG. 5 example is effectively rotated by 90 degrees. In other words the interferometer IF now performs a curved scan motion in a vertical direction (relative to the ground of the examination room) from top to bottom or from bottom to top. This is indicated in frontal view C by the arrows showing a (downward) movement of the interferometer IF during operation. Although not necessarily so in all examples, in FIG. 5 the gratings G1, G2 of the interferometer IF are now essentially arranged as strip gratings that are co-extensive of the width of the X-ray detector perpendicular to the scanning motion. Again gratings G1, G2 may be formed monolithically from single long wafer or substrate. However, in other embodiments, the strip arrangement can be achieved by tiling, that is joining together a plurality of smaller individual monolithic grating modules. The X-ray detector may be suspended in a fixture from the ceiling of the examination room or may be mounted on a floor mounted stand. The gratings G1 and G2 are rigidly mounted to a scan arm GT. Equally, the scan arm GT may be floor or ceiling mounted. The side views A) and B) show different instances during the scanning motion of the scan arm GT as it is moving along the vertical scan path in a circular or at least arcuate motion. Again, although not necessarily in all embodiments, the source grating G1 is arranged to rotate in concert about the focal spot FS. One way to do this is to have all three gratings arranged in the scan arm to maintain a fixed and parallel relationship during the vertical up or down motion. In FIG.

15 parts that move simultaneously or in concert are shown in the dashed box representing the scan arm GT. The system can easily be operated in the conventional radiography mode, by simply moving the scan arm with the gratings out of the beam. If necessary, a standard chest X-ray image can be acquired immediately before the scan can be exploited by simply swinging the scan arm out of position.

Figure 6:
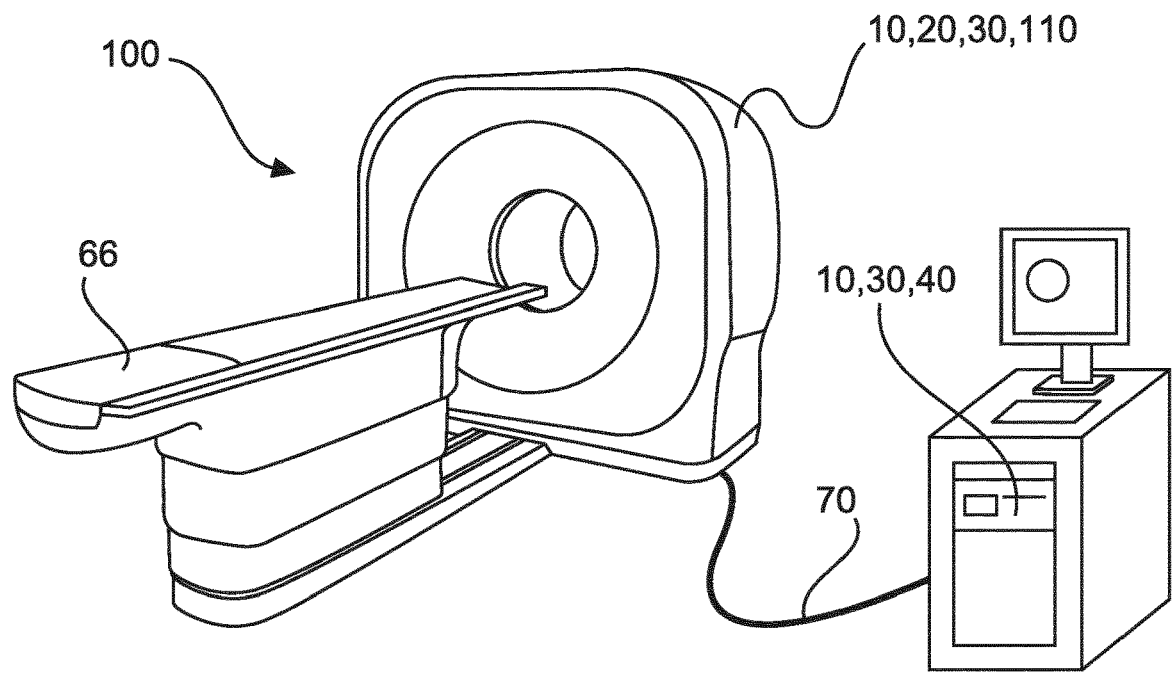
FIG. 6 shows a schematic set up of an example of a system for generating multi energy data from phase contrast imaging data.
Figure 7:
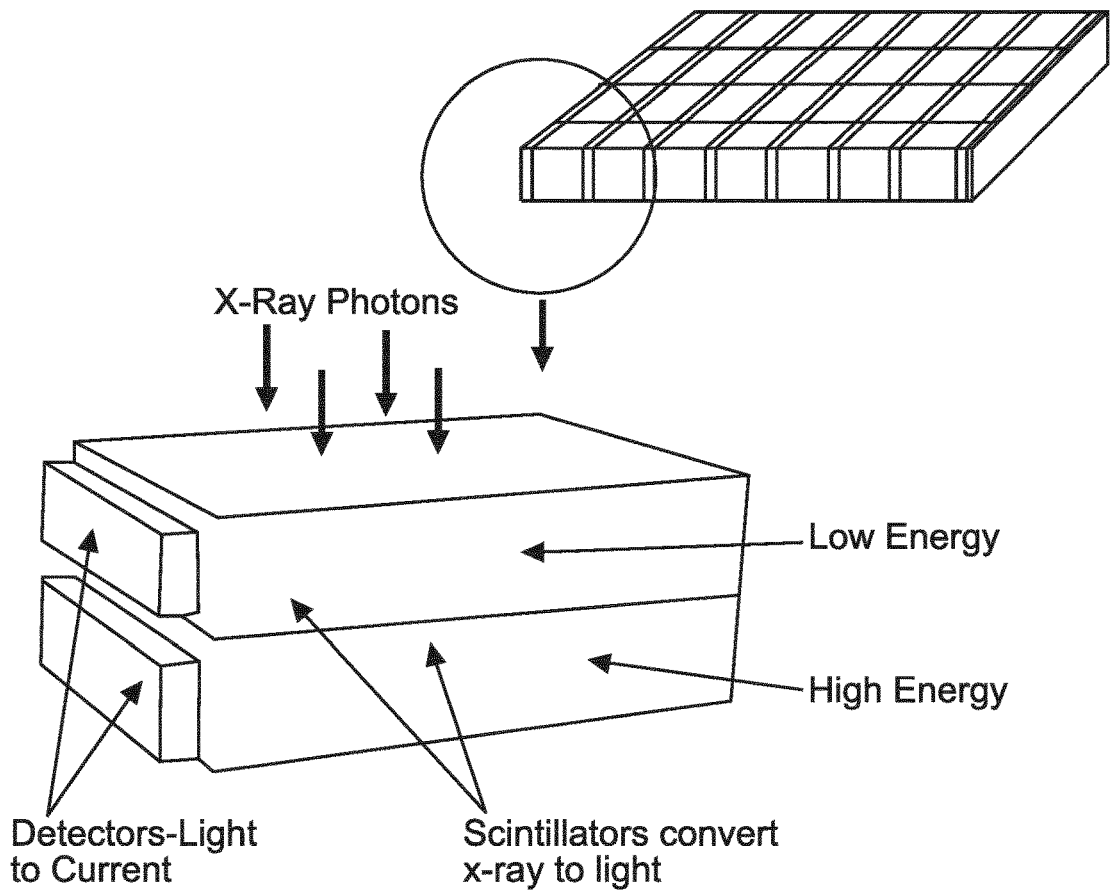
FIG. 7 shows an example of a dual energy detector.

FIG. 6 shows an example of a system 100 for generating multi energy data from phase contrast imaging data. In this example, the object is a body part of a human or animal and could be the whole body. The skilled person would however appreciate that the object could be a piece of luggage being examined at an airport or port, or be a component being examined during non-destructive testing for example. The system 100 includes an image acquisition unit 110, such as an X-ray computed tomography scanner. The system 100 is configured to generate spectral projection data and decompose that spectral data into basis sets. The system 100 shown in FIG. 6 also includes the apparatus described with respect to FIGS. 4-5, where a grating based set-up is configured to generate phase contrast images along with attenuation data and also dark field imagery. In one example, the grating based system is swung out of position, as described above with respect to FIGS. 4-5, and attenuation data is acquired. Then the grating based system is swung back into position, and phase contrast data is acquired. In another example, the attenuation data is acquired along with the phase contrast data with the grating based system. The attenuation data and the phase contrast data can then be used to generate multi energy information. However, the attenuation data can itself be spectrally resolved, through for example the use of a spectrally resolving detector as described with respect to FIG. 7. The phase contrast data is then used to generate Compton scatter data, and this is used to enrich the Compton Scatter and photoelectric data that is generated from decomposition of the spectral attenuation data. However, as would be appreciated by the skilled person, spectrally resolved data can be acquired by one system, and phase contrast data acquired by another system, and used to provide enriched multi Continuing with the system shown in FIG. 6, the image acquisition unit 110 includes one or more X-ray sources 60, such as an X-ray tube which emits radiation that traverses an examination region shown in the centre of the acquisition unit 110. The X-ray source(s) can be two X-ray sources operating at, and potentially switching between, different voltages or an X-ray source that is switching between two voltages (e.g. 80 and 100 kV, or 100 and 120 kV). The X-ray source 60 can be a source that emits broadband X-ray radiation over a range of energies. A detector 50 opposite the X-ray sources 60 detects the radiation that traverses the examination region. The detector can generate projection data for each voltage, when the source or sources are operating at different voltages at different times, or an energy resolving detector can be used to simultaneously acquire spectral projection data at different energies for two X-ray sources operating at the same time, or for a broadband X-ray source. Such an energy resolving dual layer detector is shown in FIG. 7. A patient can lie on a table which moves into the examination region, and spectral projection data of one or more body parts and indeed of the whole body if necessary can be generated/acquired. The projection data can be represented as at least one projection image (at least one spectral X-ray image). A decomposition unit, housed within the image acquisition unit or within a separate workstation, decomposes the at least one spectral X-ray image, or spectral data, into at least one basis image such as:

photoelectric attenuation image and Compton attenuation coefficient image; water and Iodine components; water and Calcium components; or acetal homopolymer resin, e.g. Delrin® and tin components; and/or other basis images.

FIG. 7 shows a dual layer detector array, which is a stack of two scintillators that are used to obtain spectral information by different effective spectral sensitivities of the layers, with one pixel of that array shown in an expanded view. A detector pixel is made from two scintillators stacked one on top of the other, with X-rays being incident from the top. Low energy X-rays are absorbed in the top scintillators, with absorption leading to the emission of longer wavelength radiation that is detected by a photodiode that is positioned on the lateral side of that scintillator. The bottom scintillator absorbs high energy X-rays and again re-emitted longer wavelength radiation is detected by a second photodiode associated with that scintillator.

In another exemplary embodiment, a computer program or computer program element is provided that is characterized by being configured to execute the method steps of the method according to one of the preceding embodiments, on an appropriate system.

The computer program element might therefore be stored on a computer unit, which might also be part of an embodiment. This computing unit may be configured to perform or induce performing of the steps of the method described above. Moreover, it may be configured to operate the components of the above described apparatus and/or system. The computing unit can be configured to operate automatically and/or to execute the orders of a user. A computer program may be loaded into a working memory of a data processor. The data processor may thus be equipped to carry out the method according to one of the preceding embodiments.

This exemplary embodiment of the invention covers both, a computer program that right from the beginning uses the invention and computer program that by means of an update turns an existing program into a program that uses invention.

Further on, the computer program element might be able to provide all necessary steps to fulfill the procedure of an exemplary embodiment of the method as described above.

According to a further exemplary embodiment of the present invention, a computer readable medium, such as a CD-ROM, is presented wherein the computer readable medium has a computer program element stored on it which computer program element is described by the preceding section.

A computer program may be stored and/or distributed on a suitable medium, such as an optical storage medium or a solid state medium supplied together with or as part of other hardware, but may also be distributed in other forms, such as via the internet or other wired or wireless telecommunication systems.

However, the computer program may also be presented over a network like the World Wide Web and can be downloaded into the working memory of a data processor from such a network. According to a further exemplary embodiment of the present invention, a medium for making a computer program element available for downloading is provided, which computer program element is arranged to perform a method according to one of the previously described embodiments of the invention.

It has to be noted that embodiments of the invention are described with reference to different subject matters. In particular, some embodiments are described with reference to method type claims whereas other embodiments are described with reference to the device type claims. However, a person skilled in the art will gather from the above and the following description that, unless otherwise notified, in addition to any combination of features belonging to one type of subject matter also any combination between features relating to different subject matters is considered to be disclosed with this application. However, all features can be combined providing synergetic effects that are more than the simple summation of the features.

While the invention has been illustrated and described in detail in the drawings and foregoing description, such illustration and description are to be considered illustrative or exemplary and not restrictive. The invention is not limited to the disclosed embodiments. Other variations to the disclosed embodiments can be understood and effected by those skilled in the art in practicing a claimed invention, from a study of the drawings, the disclosure, and the dependent claims.

In the claims, the word "comprising" does not exclude other elements or steps, and the indefinite article "a" or "an" does not exclude a plurality. A single processor or other unit may fulfill the functions of several items re-cited in the claims. The mere fact that certain measures are re-cited in mutually different dependent claims does not indicate that a combination of these measures cannot be used to advantage. Any reference signs in the claims should not be construed as limiting the scope.

The invention claimed is:

1. An apparatus for generating multi energy data from phase contrast imaging data, comprising:
   an input unit; and
   a processing unit;
   wherein the input unit is configured to provide the processing unit with phase contrast X-ray image data of a region of interest of an object;
   wherein the input unit is configured to provide the processing unit with attenuation X-ray image data of the region of interest of the object;
   wherein the processing unit is configured to generate multi energy data comprising two basis data sets;
   wherein the processing unit is configured to generate a first basis data set from the phase contrast X-ray image data, wherein the first basis data set comprises Compton data, the Compton data corresponding to Compton scattering total attenuation coefficient data;
   wherein the processing unit is configured to generate a second basis data set from the phase contrast X-ray image data and the attenuation X-ray image data after the generation of the first basis data set, wherein the second basis data set comprises photoelectric data, the photoelectric data corresponding to photoelectric total attenuation coefficient data;
   wherein generation of the second basis data set comprises utilization of the first basis data set, wherein the attenuation X-ray image data is utilized with the Compton scattering total attenuation coefficient data to calculate the photoelectric total attenuation coefficient data; and
   wherein the processing unit generates the first basis data set on a basis that the phase contrast X-ray image data at an image location is proportional to the first basis data set at the image location.

2. The apparatus according to claim 1, wherein a spectral detector sensitivity of a detector used to acquire the phase contrast X-ray image data is the same as a spectral detector sensitivity of a detector used to acquire the attenuation X-ray image data; and wherein a baseline intensity signal relates to a detected signal on the detector when the object is not present; and wherein a spectrum of an X-ray source used during the acquisition of the phase contrast X-ray image data is the same as a spectrum of an X-ray source used during the acquisition of the attenuation X-ray image data; and wherein generation of the second basis data set comprises utilization of the spectral detector sensitivity of the detector and the baseline intensity signal and the spectrum of the X-ray source.

3. The apparatus according to claim 1, wherein the attenuation X-ray image data comprises spectral image data.

4. The apparatus according to claim 1, wherein the phase contrast X-ray image data and the attenuation X-ray image data were acquired at a same time.

5. The apparatus according to claim 1, wherein the processing unit is configured to generate multi energy and/or dual energy information on a basis of the first basis data set and second basis data set, the information comprising at least one image of the region of interest of the object.

6. A system for generating multi energy data from phase contrast imaging data, the system comprising:
   at least one image acquisition unit;
   the apparatus for generating multi energy data from phase contrast imaging data according to claim 1; and
   an output unit;
   wherein, the at least one image acquisition unit is configured to acquire the phase contrast X-ray image and to acquire the attenuation X-ray image; and
   wherein, the output unit is configured to output multi energy and/or dual energy information on the basis of the first basis data set and the second basis data set.

7. The apparatus according to claim 2, wherein generation of the second basis data set comprises utilization of an energy dependence relating to data of the first basis data set and an energy dependence relating to data of the second basis data set.

8. The apparatus according to claim 2, wherein the detector used to acquire the phase contrast X-ray image data is the same as the detector used to acquire the attenuation X-ray image data; and wherein the X-ray source used during the acquisition of the phase contrast X-ray image data is the same as the X-ray source used during the acquisition of the attenuation X-ray image data.

9. The apparatus according to claim 3, wherein the processing unit is configured to decompose the spectral image data into at least one basis image, the at least one basis image comprising a first basis data set image.

10. A method for generating multi energy data from phase contrast imaging data, comprising:
    providing phase contrast X-ray image data of a region of interest of an object;
    providing attenuation X-ray image data of the region of interest of the object;
    generating a first basis data set from the phase contrast X-ray image data, wherein the first basis data set comprises Compton data, the Compton data corresponding to Compton scattering total attenuation coefficient data; and
    generating a second basis data set from the phase contrast X-ray image data and the attenuation X-ray image data after the generation of the first basis data set, wherein the second basis data set comprises photoelectric data, the photoelectric data corresponding to photoelectric total attenuation coefficient data, and further comprising utilizing the first basis data set, wherein the attenuation X-ray image data is utilized with the Compton scattering total attenuation coefficient data to calculate the photoelectric total attenuation coefficient data;

wherein the first basis data set is generated on a basis that the phase contrast X-ray image data at an image location is proportional to the first basis data set at the image location.

11. A computer program element embedded in a non-transitory computer readable medium for controlling an apparatus, the computer program element when executed by a processor is configured to carry out a method comprising:

providing phase contrast X-ray image data of a region of interest of an object;

providing attenuation X-ray image data of the region of interest of the object;

generating a first basis data set from the phase contrast X-ray image data, wherein the first basis data set comprises Compton data, the Compton data corresponding to Compton scattering total attenuation coefficient data; and generating a second basis data set from the phase contrast X-ray image data and the attenuation X-ray image data after the generation of the first basis data set, wherein the second basis data set comprises photoelectric data, the photoelectric data corresponding to photoelectric total attenuation coefficient data, and further comprising utilizing the first basis data set, wherein the attenuation X-ray image data is utilized with the Compton scattering total attenuation coefficient data to calculate the photoelectric total attenuation coefficient data;

wherein the first basis data set is generated on a basis that the phase contrast X-ray image data at an image location is proportional to the first basis data set at the image location.

\* \* \* \* \*